United States Patent [19]
Nadler et al.

[11] 4,405,216
[45] Sep. 20, 1983

[54] GLARE SUSCEPTIBILITY TESTER

[75] Inventors: M. Princeton Nadler, Sewickley, Pa.; David Miller, Boston, Mass.

[73] Assignee: Mosebach Electric & Supply Company, Pittsburgh, Pa.

[21] Appl. No.: 265,403

[22] Filed: May 20, 1981

[51] Int. Cl.³ .................. A61B 3/02; A61B 3/00
[52] U.S. Cl. .................. 351/237; 351/243
[58] Field of Search .................. 351/17, 30, 36

[56] References Cited

U.S. PATENT DOCUMENTS 1,780,291  11/1930  Cameron .................. 351/36
3,684,355  8/1972  Mohner .................. 351/36

OTHER PUBLICATIONS

A brochure entitled "Compact Acuity Projector" Cat. No. 71-34-40 instructions by Bausch & Lomb, Rochester, New York.
A brochure entitled "B.VAT Video Acuity Tester" by Codman & Shurleff, Inc., Randolph, Massachusetts.

Primary Examiner—John K. Corbin
Assistant Examiner—Rodney B. Bovernick
Attorney, Agent, or Firm—Buell, Blenko, Ziesenheim & Beck

[57] ABSTRACT

An apparatus for testing glare susceptibility of a subject. A planar member having an opaque target is surrounded by a contrasting surface which is surrounded by a translucent surface. Light is directed to one side of the planar member and the subject's ability to see the target against the contrasting surface against a glare of light through the translucent surface determines the glare susceptibility of the subject.

4 Claims, 3 Drawing Figures

GLARE SUSCEPTIBILITY TESTER

BACKGROUND AND PRIOR ART

One aspect of the ability of a person to see an object is sensitivity to glare. Ophthalmologists and optometrists determine sensitivity to glare by shining a small light in the patient's eye and making a skilled judgment as to whether the patient is more or less sensitive to glare.

U.S. Pat. No. 3,684,355 discloses a glare tester which uses a series of targets on a film strip. A source of light illuminates the target and the same source of light passes through filters to provide a variable glare to the eye. The patent also shows another form of glare tester in which light is passed through filters and varies the illumination of a target. A separate circular light surrounding a port provides a source of glare. A separate glare shield ring prevents light from the annular ring illuminating the target. These devices rely upon varying the illumination of the target image or the amount of glare. The filter strips and the target strips must be coordinated and the device is complex because of all the moving parts and the necessary coordination of the different separate film strips and target.

The inventors have provided a simpler tester by using a plurality of unique slides in a standard Fairchild Syncro-Slide 35 Projector Model No. 3501 which is simple to operate and inexpensive. The cost is reduced because of the adaptability of the concept to the use of a standard slide projector. The concept could be used with any other standard slide projector having its own screen.

We provide a glare susceptibility testing device comprising: A planar member having target image on its surface, a contrasting surface surrounding the target image and which provides a contrast with the target when light is directed to the target and the contrasting surface and a translucent surface surrounding the contrasting surface; and means supporting the planar member and directing light to one side of the planar member.

Other details, objects and advantages of this invention will become apparent as the following description of the present preferred embodiment proceeds.

DESCRIPTION OF THE INVENTION

Figure 1:
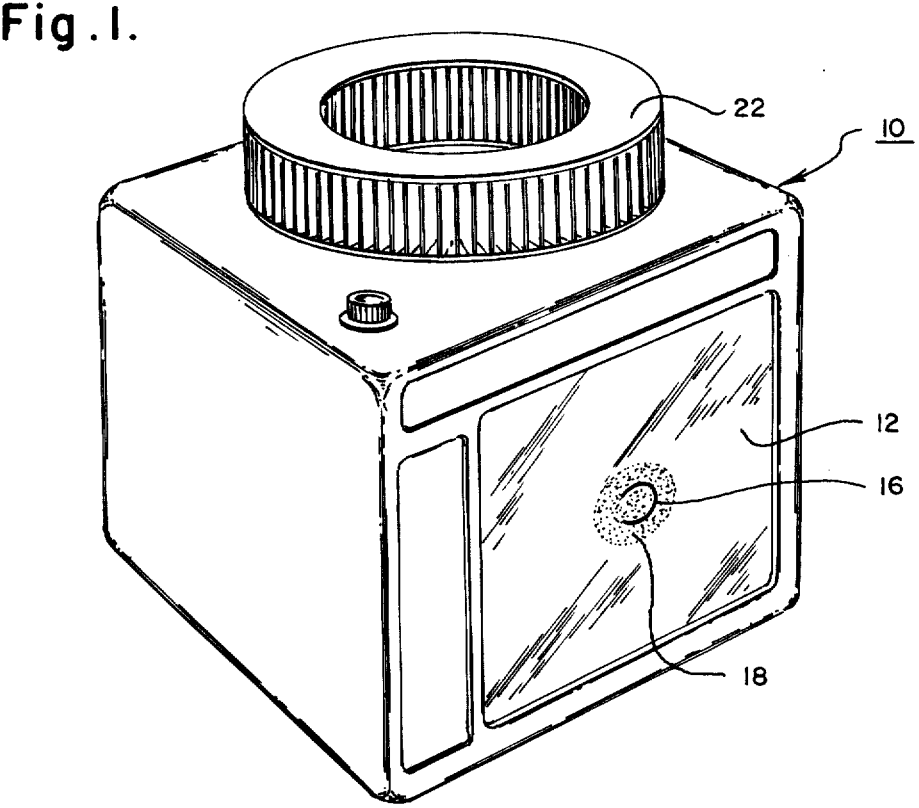
FIG. 1 is an isometric view showing the glare tester.

FIG. 1 shows a glare tester. The tester has a standard Fairchild Syncro-Slide 35 Projector Model No. 3501 shown generally 10. The projector has a screen 12 which projects a slide of the type shown in FIGS. 2 and 3.

The slide 14 is a planar member having: An opaque Landolt target image 16 on its surface; contrasting surface 18, 18' and 18" surrounding the target image 16 which provides a contrast with the target 16 when light is directed to one side of the target 16 from the projector; and a translucent surface 20 which diffuses the light from the projector and surrounds the contrasting surface 18, 18' and 18". The projector 10 supports a carrousel of slides in which the contrasting surface 18, 18' and 18" varies in contrast density among the slides from a contrast of 2.5% to 80% from the opaque Landolt target 16. The density of the Landolt target 16 remains constant among the slides. The translucent properties of the translucent surface 20 remains constant thereby providing a constant source of glare to the eye from the screen 12 against which the visual perception of the Landolt target 16 can be measured against the varying density of the contrasting surface 18, 18' and 18" from slide to slide.

When projected on the screen 12 after magnification, the diameter of the Landolt ring target 16 is 0.9 cm.; the diameter of the contrasting surface 18 is 3.0 cm. and the dimensions of the translucent surface 20 are 23 cm. × 16 cm. The Landolt ring targets when projected on the screen have 20/400 Snellen equivalent size. The translucent surface projected on the screen of the projector provides a diffuse glare source which has proven superior to a point of light glare source because it does not distract attention from the dominant central target 16.

OPERATION

Figure 2:
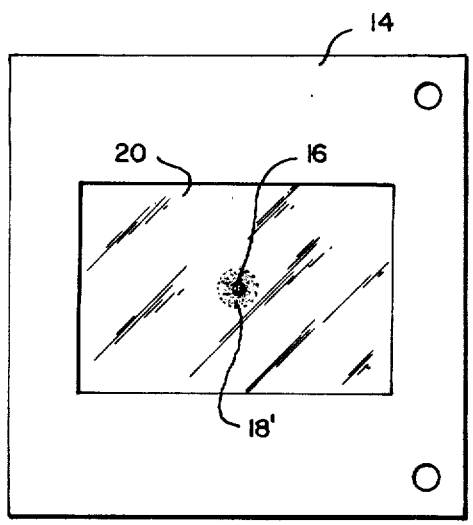
FIG. 2 is a front view of a slide.
Figure 3:
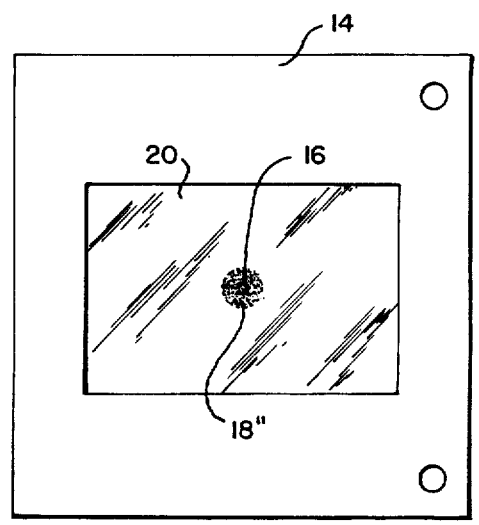
FIG. 3 is a front view of another slide.

In operation the slides are shown to a patient in a sequence with the contrasting surface 18 going from a light background to a dark background which permits one to easily distinguish the opaque Landolt ring target 16 from the lighter contrasting surface 18 and the darker contrasting surface which makes it more difficult to distinguish. This sequence is shown in FIGS. 2 and 3 which show varying degrees of contrasting surfaces 18' and 18". The contrasting surface 18 becomes progressively darker by succeeding slides until the contrast threshold between the contrasting surface 18 and the opaque Landolt ring target 16 is reached. The end point of the test is recorded as the last identified slide.

This tester now enables the clinician to test and quantify glare sensitivity. It can be helpful, preoperatively, in justifying corneal, cataract and vitreous surgery. Postoperatively, it can be helpful as a means of measuring the success of such surgery distinct from Snellen acuity.

The contrasting surface 18 is photographically reproduced using gelatin neutral density filters varying from 0.70 to 3.00 in value.

The slides may be photographed for presentation in any one of four orientations within the carrousel 22 which holds approximately 30 slides, more or less, with a varying contrasting surface density. Patients are positioned 14 inches from the screen 12 with the eye directly facing the projection of the Landolt ring target. At this viewing distance the Landolt ring subtends 1 degree 16.7' producing the equivalent of a 20/400 Snellen letter.

The slide calibration can be made as follows: Percent contrast (C) is defined as:

$$C = \frac{L_{max} - L_{min}}{L_{max} + L_{min}} \times 100$$

where $L_{max}$ = maximal luminance (the surround)
$L_{min}$ = minimal luminance (the target)

Thus, contrast may theoretically be as low as zero, (when the luminance of two objects compared are equal). This can only happen if $L_{min} = 0$ (i.e. absolute flat black). It may theoretically go up to 99.9., also.

We claim:
1. A glare susceptibility testing device comprising:
   a a plurality of planar members each member having:
      (i) a target image approximately centrally located on its surface;

(ii) a contrasting surface adjacently surrounding the target image and which provides a contrast with the target when light is directed to the target and the contrasting surface, each contrasting surface of each member varies from the contrasting surface of the other members; and (iii) a translucent surface adjacently surrounding the contrasting surface; and b. means supporting the planar member and directing light through the planar member to produce an image of the target and contrasting surface which is totally surrounded by a glare source produced by the light.

2. A glare susceptibility testing device as recited in claim 1 wherein the target image is essentially opaque.

3. A glare susceptibility device as recited in claim 2 wherein the target is a Landolt ring which varies in orientation among the plurality of panel members.

4. A glare susceptibility testing device as recited in claim 3 wherein the Landolt ring has a diameter of 0.9 cm. and the contrast surface spans a distance in one direction of 3 cm. and the translucent surface spans an area of 16 cm. ×23 cm.

* * * * *